United States Patent [19]

Walker et al.

[11] Patent Number: 4,822,362

[45] Date of Patent: Apr. 18, 1989

[54] PROCESS AND APPARATUS FOR TIBIAL PLATEAU COMPENENT

[76] Inventors: Peter S. Walker, 15 Hallett Hill Rd.; Frederick C. Ewald, 4 Black Oak Rd., both of Weston, Mass. 02193

[21] Appl. No.: 52,033

[22] Filed: May 19, 1987

[51] Int. Cl.[4] .......................... A61F 2/38; A61F 5/04; F24C 15/20

[52] U.S. Cl. ................. 623/20; 128/92 VW; 128/92 VD; 128/303 R

[58] Field of Search ................ 623/20, 18; 128/92 R, 128/92 V, 92 VY, 92 VW, 92 VV, 92 VW, 92 VD, 316, 305, 303 R

[56] References Cited

U.S. PATENT DOCUMENTS

| | | | |
|---|---|---|---|
| 3,869,729 | 3/1975 | Attenborough | 623/20 |
| 3,918,101 | 11/1975 | Lagrange et al. | 623/20 |
| 3,934,272 | 1/1976 | Wearne et al. | 623/20 |
| 3,958,278 | 5/1976 | Lee et al. | 623/20 |
| 4,136,405 | 1/1979 | Pastrick et al. | 623/20 |
| 4,216,549 | 8/1980 | Hillberry et al. | 623/20 |
| 4,219,893 | 9/1980 | Noiles | 623/20 |
| 4,257,129 | 3/1981 | Volz | 623/20 |
| 4,711,639 | 12/1987 | Crundei | 623/20 |

FOREIGN PATENT DOCUMENTS

| | | | |
|---|---|---|---|
| 0010527 | 4/1980 | European Pat. Off. | 623/20 |
| 2122390 | 1/1973 | Fed. Rep. of Germany | 623/20 |
| 3334531 | 8/1985 | Fed. Rep. of Germany | 623/20 |
| 2465470 | 4/1981 | France | 623/20 |

*Primary Examiner*—Richard J. Apley
*Assistant Examiner*—David J. Bender
*Attorney, Agent, or Firm*—Wolf, Greenfield & Sacks

[57] ABSTRACT

A prosthesis and a surgical procedure (process) therefore are provided having a relatively thin plate fitted to a resected portion of the tibial plateau with the plate fitting uniformly around a major portion of the calcareous bone of the cortical wall. A pin on the under side of the plate aligned substantially with the axis of the intramedullary canal of the tibia fixes the plate against transverse relative motion between the plate and plateau, and blades or keels also on the under side of the plate are aligned maximum density (strength) of the cancellous bone of the plateau and fix the plate against rotation relative to the plateau. The surgical procedure of the invention employs a template to assure approximate positioning, and exact interrelationship between the plate and the fixing means.

8 Claims, 2 Drawing Sheets

PROCESS AND APPARATUS FOR TIBIAL PLATEAU COMPENENT

FIELD OF THE INVENTION

The present invention relates to prostheses for human joints and more particularly to prostheses of the knee and to a process (surgical procedure) of applying the same. Still more particularly it relates to a tibial component of a knee prosthesis and a process of applying same.

BACKGROUND OF THE INVENTION

The human knee joint is subjected to the greatest pressures of any joint in the body. This is because it must bear the full weight of the body with disadvantageous leverage ratios. Thus, at times when, for example, a person is rising to a standing position from a sitting position, or going up stairs, the actual forces at the interface between the components of the knee joint will be many times the weight of the person. This places a premium on the design of a prosthesis both for resistance to the forces applied across the joint and to accommodate the wear in the prosthesis which inevitably results from such pressures.

In addition, in the application of prostheses of any sort it is important to avoid resecting any more of the joint than necessary. This is especially true of the knee which includes ligaments within the joint, i.e., the cruciate ligaments which are important for the future functioning of the joint, and, therefore, in the design of the prosthesis it is important to keep the thickness of the prosthesis to a minimum so as to avoid resection, but yet to do so without sacrificing consistent and long term adequate performance.

Other factors in addition come into play in the design of a knee prosthesis such as the need to anchor it against the forces of shear, tipping, and torque to which the knee joint is particularly subjected.

Further, there is a need for standardization of manner in which the prosthesis is applied, and to provide mechanisms by which the preparation of the tibial plateau for application of the prosthesis is done in such a way as to make the excisions fit with the components to be applied to the plateau.

Accordingly, it is an objective of this invention to provide a tibial component for a prosthesis of the knee which is designed to provide maximum support against the compressive forces across the joint, as well as a concomitant maximum resistance to wear. Still another objective is to provide such a tibial component which takes up a minimum of thickness thereby reducing the requirements for resection, but yet which provides a maximum balance between strength and longevity. Still another objective is to provide such a tibial component with a firm supporting base relative to the tibial plateau, and to be anchored maximally for resistance to shear, bending, tipping and torque forces. Still another object is to provide a method for the application of such a prosthesis which assures the accurate excision of portions of the tibial plateau so as to fit the prosthesis components and thereby assure a close, strong, and long lasting fit between the prosthesis and the tibial plateau of the patient.

SUMMARY OF THE INVENTION

In the accomplishment of these and other objects of the invention, in a preferred embodiment thereof, a relatively thin base plate of suitable metal, is contoured and dimensioned to correspond substantially to the peripheral size and shape of the tibial plateau of the joint, and to extend in all directions to cover and rest close to the (calcareous) cortical wall for a major part of the circumference thereof. The bony plateau is preferably trimmed and excised to make it fit the undersurface of the plate. A fixation pin is mounted on the under surface of the base plate in substantially axial alignment with the medullary or intramedullary canal of the tibia and dimensioned to extend down into the tibia when the plate is in abutment with the plateau to a point close to (or even reaching) the upper end of the canal. Prior to insertion, a cylindrical core is bored into the cancellous bone roughly on the axis of the canal to provide room for insertion of the fixation pin.

In order to fix the plate against shear, tipping and torque, anchoring means are provided on the under surface of the plate comprising projections located relative to the plateau to enter at approximately the centers of each of the lateral areas of the plateau, which are regions of maximum hardness of the cancellous bone. Normally there are two such areas set to each side of the axis of the canal and on a line about 20 degrees the rear of the median transverse plane of the joint which passes through the axis of the canal. These areas of maximum hardness occur towards the peripheral cortical wall of the tibia. The plateau is prepared to receive the projections by cutting appropriately located slots in the cancellous bone. The projections take the form of keels, which are preferrably joined to the fixation pin by webs which serve to support the base plate against bending forces between the fixation pin and the blades or keels.

To provide a suitable long wearing surface, a plastic cap is provided for the base plate, having a concave upper surface suitable to receive and support condylar elements of the joint. Also, in order to provide maximum thickness for the plastic, but at the same time to occupy a minimum of vertical height for the prosthesis, recesses are provided in the plate in the areas immediately above the blades(keels), over the areas of maximum hardness of the cancellous bone of the plateau. These areas are, of course, the areas where the maximum condylar forces are applied. The recesses provide additional thickness of plastic at those places, whereas the areas in the plate surrounding the recesses, maximum metal is provided for strength.

Overhanging ledges are provided at the back and front of the upper surface of the plate for securing the plastic cap to the plate by a safe snap fit. This permits using plastic elements of different thicknesses with the same base.

The posterior central region of the plate and plastic cap are also recessed to provide clearance for the posterior cruciate ligament to pass upwardly through the rear part of the plate (and also to provide a path for fluids to pass from the cancellous bone to enter the joint, or for debris to leave it).

The process of surgically installing the invention entails the use of a template having a hollow central guide tube for the purpose of locating the correct places for incission into the tibial plateau and for guiding the direction of the incisions. The steps comprise, first, resecting the upper tibia, carefully avoiding the ligaments to make the plateau flat and to expose the cancellous bone, including the strong (calcareous) regions noted above, and the thin rim of cortical bone. Next, a corer is driven down through a guide tube of a template into the cancellous bone of the plateau, substantially along the axis line of the intramedullary canal. The depth of the hole is preferably taken down near to the upper end of the canal. The bone which is now in the hollow tube of the corer is forced down into the bone canal where it serves as a plug at the bottom of the hole to prevent or hinder the escape of cement which may be inserted at the time of applying the base plate of the prosthesis to the tibial plateau. The corer also includes a pair of lateral cutter blades which are lowered into the template simultaneously with the descent of the corer and are guided in slots in the quide tube of the template so as to penetrate at the correct angles for location of the fixing blades. These cutter blades are driven in at the same time as the core is being taken, and they provide accurately located slots to recieve the keels of the implant. In addition, since the template is resting on the flat resected surface of the tibia, the guide tube of the template assures that the core and hence the fixation pin will be at precisely 90 degrees with respect to the tibial surface. This is extremely important because even a small deviation of the angle of the pin from perpendicular to the plane of the plate as it is resting on the upper tibial surface will set up an uneven stress distribution on the tibial surface and high stresses on the tibial component which could lead to eventual breakdown.

It is a feature of the invention that the outer edges of the base plate are close to the peripheral cortical wall around a major portion of the circumference of the joint. Another feature is that the central fixation pin of the plate enters the plateau substantially along the optimal line of axis of the intramedullary canal of the tibia to provide general fixation support and to enable extension to a longer intramedullary stem if necessary. It is also a feature that the plate is fixed against shear, tipping, and torque forces by keels entering the plateau at the point of maximum hardness of the cancellous bone, and also that there is the least possible resection especially in areas of maximum density in cancellous bone. It is still another feature that the plate is reinforced against bending between the fixation pin and the blades or keels. In addition, these features are accomplished in the context of a tibial plateau plate and plastic cap combination in which maximum thickness of plastic is provided in the areas of maximum pressure and wear, whereas additional thickness of metal is provided outward of the areas of maximum pressure in order to reinforce the plate against bending stresses. Thus, the objectives of minimum vertical dimension and maximum performance are obtained.

The features of the process of the invention are that the surgeon can perform the resection of the upper surface of the tibial plateau, the coring of the central hole and the incission of the slots for the blades or keels quickly and with assurance that he is locating them precisely and correctly in relation to each other and to the rim of the cortical wall. Also he can perform these tasks with a minimum of removal of tissue and/or bone, and thereby provide as efficient and secure a prosthesis as possible.

BRIEF DESCRIPTION OF THE DRAWINGS

An embodiment of the invention selected for purposes of illustration only is shown in the accompanying drawings is which.

DETAILED DESCRIPTION OF THE INVENTION

Figure 1:
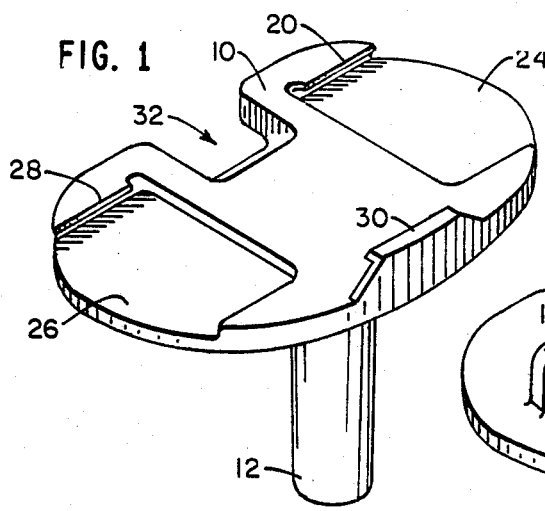
FIG. 1, is a perspective view from above and to the side showing the upper surface of the base plate of the invention without the plastic cap mounted on top.
Figure 2:
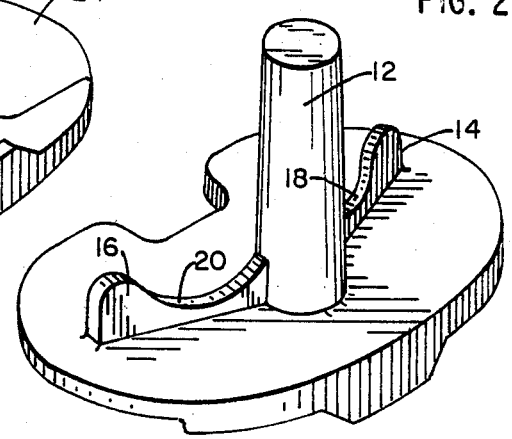
FIG. 2, is a perspective view from underneath of the base plate showing the central fixation pin, the anchoring keels and the webs therebetween.
Figure 3:
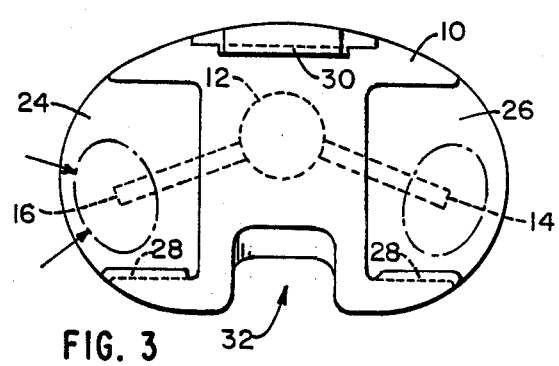
FIG. 3, is a plan view of the base plate.

The embodiment of the invention selected for purposes of illustration comprises, a base plate 10 of suitable metal, preferably a cobalt-chromium-molybdenum alloy corresponding to ASTM specification F75, sometimes sold under the trademark "VITALLIUM", or a titanium-6aluminum4vanadium alloy. The base plate 10 is contoured and dimensioned to correspond substantially to the size and shape of the tibial plateau of the joint. In practice, it is made in a range of sizes. The size selected in any particular case is such that the periphery of the plate will extend to the outer rim of the upper tibia for a major part of the circumference thereof.

In use the plate 10 is mounted on a tibial plateau which has been preferably trimmed in advance to make it correspond to the flat undersurface of the plate. A slightly tapered fixation pin 12 is mounted integrally on the under surface of the plate in general axial alignment with the intramedullary canal of the tibia and dimensioned to extend down into the tibia when the plate is in abutment with the plateau, to a point close to (or even reaching) the upper end of the canal. The fixation pin 12 can be hollow to accommodate an extension stem if desired, or an extension stem can be pressed over the pin itself. Prior to insertion, a cylindrical core hole is bored into the cancellous bone on the axis of the canal to provide room for insertion of the fixation pin 12.

In order to further secure the plate against shear, tipping and torque forces, anchoring means are provided on the under surface of the plate comprising projections 14, 16 located relative to the plateau to enter the surface of the plateau at approximately the centers of each of the areas of the plateau of maximum hardness of the cancellous bone, and generally in the region where the contact forces are most commonly applied. Normally there are two such areas set laterally of the axis of the canal and on a line about 20 degrees to the rear of the transverse plane of the joint which passes through the axis of the canal. These areas of maximum hardness also occur towards the peripheral cortical wall of the tibia. The surface of the bone is prepared to receive the projections 14, 16 by cutting slots in them. The projections 14, 16 may take the form of keels, and preferably they are joined to the fixation pin 12 by shallow webs 18, 20 respectively which serve to support the base plate against bending forces between the fixation pin 12 and the blades 14, 16.

To provide a suitable long-wearing and low-friction surface, a plastic cap 22 is provided for the base plate, having a concave upper surface suitable to receive and support condylar elements of the joint (which can be either natural or prosthetic). The plastic is preferably a high molecular weight polyethylene as for example that sold under the designation "RCH 100" by the American Hoechst company. In order to provide maximum thickness for the plastic in the areas of maximum pressure and wear, but at the same time to assure that the plate will occupy a minimum of vertical height for the prosthesis, recesses 24, 26 are provided in the plate in the areas immediately above the blades 14, 16, over the areas of maximum hardness of the cancellous bone of the plateau. In this way, the recesses provide additional thickness of plastic at those places, whereas in the areas in the plate surrounding the recesses, maximum metal is provided for strength.

Figure 6:
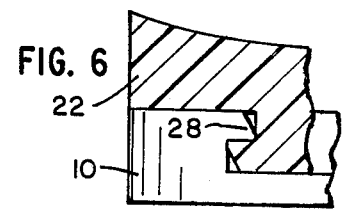
FIG. 6, is an enlarged view of the left hand circled portion of FIG. 5.
Figure 7:
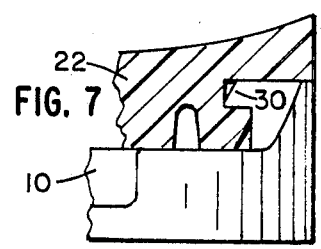
FIG. 7, is an enlarged view of the right hand circled portion of FIG. 5.
Figure 4:
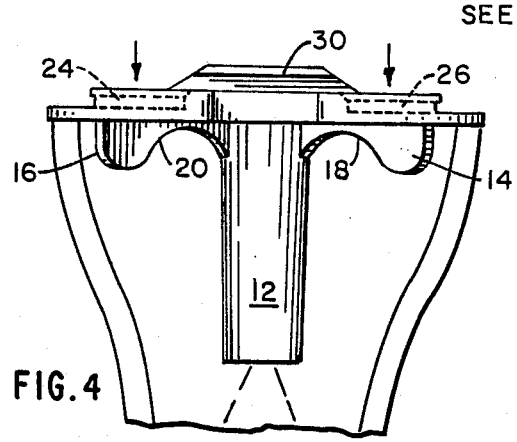
FIG. 4, is a view in rear elevation of the base plate diagrammatically showing the base plate mounted on a tibial plateau.
Figure 5:
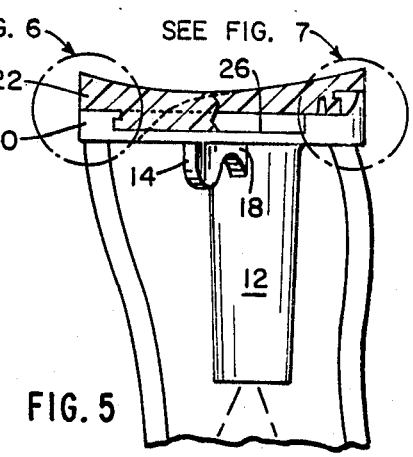
FIG. 5, is a view in side elevation of the base plate and diagrammatic representation of FIG. 4.
Figure 8:
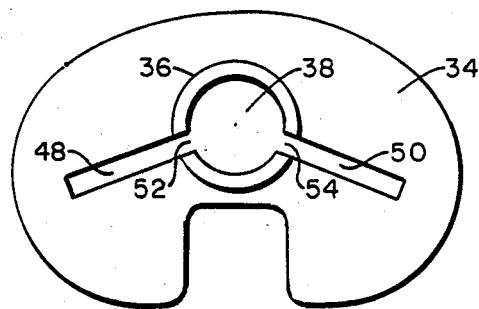
FIG. 8, is a plan view of the template used in the process of the invention.
Figure 11:
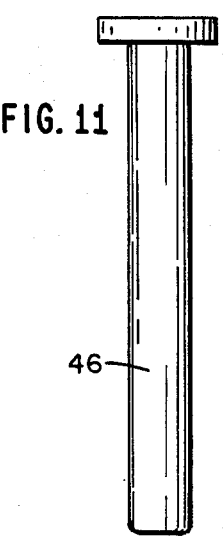
FIG. 11, is a side view of the rod used to force the cored plug of cancellous bone out of the corer and into the cavity in the tibial plateau.
Figure 9:
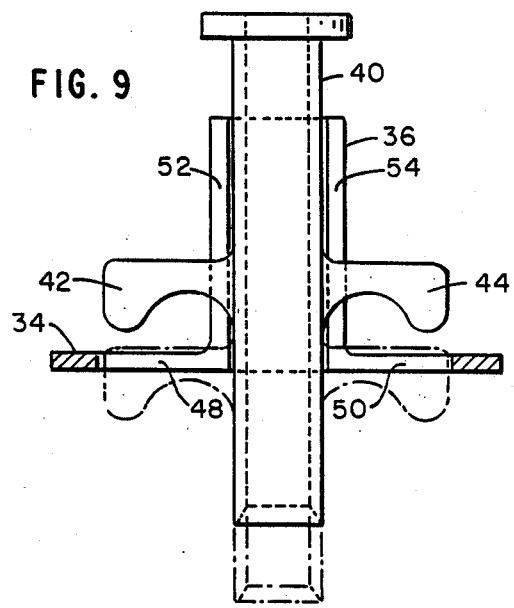
FIG. 9, is a view in rear elevation of the template of FIG. 8; and the cover used with the template in the process of the invention
Figure 10:
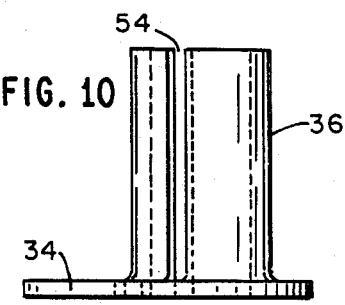
FIG. 10, is a view in side elevation of the template of FIG. 8.

Overhanging ledges 28 in the rear, and 30 in the front are provided in the upper surface of the plate for securing the plastic cap to the plate by a safe snap fit (see Figs. 5, 6, and 7).

The posterior edges of the plate 10 and cap 22 are provided with a u-shaped recess 32 dimensioned to provide an unobstructed path for the posterior cruciate ligament (which preferably is not resected in the use of the prosthesis of the present invention) so that the ligament can pass through the plate from the posterior upper part of the tibial plateau forward to the anterior part of the femur.

Since the central fixation pin 12 is substantially on the optimal line of axis for fixation to the tibia, i.e., on the axis of the intramedullary canal of the joint, the prosthesis is secured to the tibia in the preferred location for survival of the prosthesis. It is also secured optimally against shear, tipping, and torque forces by supporting the rim of the plate 10 substantially over the entire upper surface of the tibia up to the cortical wall around a major portion of the joint and by locating the blades 14, 16 at the points of maximum hardness of the cancellous bone. In addition the webs 18, 20 reinforce the plate against bending forces therebetween. Further, these features are accomplished in the context of a tibial plateau plate and plastic cap combination in which maximum thickness of plastic is provided in the areas of maximum pressure, whereas additional thickness of metal is provided outwardly of the areas of maximum pressure in order to reinforce the plate against bending stresses. Thus, the objectives of minimum vertical dimension and maximum performance are obtained with the least possible sacrifice of either. In addition, since the plate fits uniformly against the rim of the cortical wall around a major portion of the circumference, since the maximum points of pressure against the plate are supported at the points of maximum hardness (strength) of the cancellous bone, and since the prosthesis is anchored from the possibility of slipping or turning by the blades or keels also located at those same places, the combination is optimally arranged to remain fixed in the desired position.

The prosthesis can be affixed to the tibial plateau by various means including by cement or by a press-fit. The method of application employs a template 34 having integrally mounted on it a hollow central guide tube 36. The template 34 is substantially the same size and shape as the base plate 10 and is designed to approximate the tibial plateau to which the prosthesis is to be applied, and the guide tube 36 is located so that its central hole 38 is in alignment with the intramedullary canal of a normal or average subject. The guide tube 36 is dimensioned to receive a corer 40 the diameter of which is substantially the same as that of the fixation pin 12. The corer 40 also has mounted integrally on its sides a pair of cutter blades 42, 44 which correspond in size shape and relative position to the blades 14, 16 on the base plate 10. Guide tube 36 is slotted at 52, 54 to receive the cutter blades 42 and the template is also slotted at 48, 50 likewise to receive the cutter blades when the corer is lowered fully into the template.

In operation, the template is placed onto the trimmed and flattened tibial plateau with its rim close to the cortical wall around a major portion of its circumference. Then with all in place, the corer 40 is put into the guide tube 34 and driven down into the tibial plateau taking a core of the cancellous bone at the appropriate place for the pin 12 and simultaneously driving the cutter blades 42, 44 through the slots 48, 50 and into the tibial plateau at the appropriate locations for the blades 14, 16 relative to the pin 12 and plate 10. Thereafter, the core of removed cancellous bone is driven further down into the intramedullary canal by means of a pin 46, where the bone material can serve usefully to form a plug so as to retain the cement which may be used to fix the prosthesis to the tibia. Otherwise, the pin 12, may be slightly tapered and the corer have a slightly smaller diameter than the pin 12 such that the prosthesis can be fixed in place by a snug, press-fit which is preferrable for some applications.

The advantages of the process are that an extremely secure prosthesis is provided with all components accurately fitting each other and without introducing residual or unwanted stresses between the prosthesis and the tibia. This is done at the expense of a small sacrifice with respect to the position of the blades 14, 16 and the pin 12, but with the far greater advantages of being assured that each component is precisely located with respect to the portions of the tibial plateau which have been excised to receive them.

Having thus described an illustrative embodiment of the invention, various modifications thereof will now become apparent to those skilled in the art. For example, the blades 14, 16 need not be planar, but can equally well be in the shape of pins. The angle of the blades 14, 16 need not be precisely 20 degrees but can vary +/− by about 10 degrees. Accordingly, it is not intended to confine the invention to the precise form herein shown but rather to limit solely in terms of the appended claims.

We claim:

1. Apparatus for preparing a tibial plateau of a human knee joint for mounting a plate-like tibial prosthetic component thereon, which component comprises:

a plate having an upper and an under surface, said plate having substantially the same size and shape as the tibial plateau on which it is to be mounted with gap along its posterior edge to accomodate the passage of the posterior cruciate ligament of said joint;

means mounted on the upper surface of said plate adapted to recive and support condylar portions of said joint;

means on the under surface of said plate for fixing said plate against lateral shifting on said plateau comprising a pin located substantially on the line of the intramedullary canal of said tibia and dimensioned to occupy and extend into only the least dense area of the cancellous bone of said plateau to a depth at least near to the upper end of said canal; and means of the under surface of said plate for fixing said plate against rotation relative to said plateau comprising a projection located in each of the areas of said plateau where the cancellous bone is most dense, said projections dimensioned to occupy only a minor portion of said most dense areas, said apparatus comprising:

a template having an upper and a lower surface and having the same size and shape as said plate;

a hollow guide tube mounted on the upper surface of said template at a location corresponding to the location of the pin on the under surface of said plate, said guide tube having an inside diameter substantially the same as the outside diameter of said pin;

walls forming slots in said guide tube longitudinally thereof set at the same angle from the axis of said tube as said projections are set from the axis of said pin on the under surface of said plate;

walls forming slots in said template corresponding in size, shape and location to said projections on the under surface of said plate; and means for use in conjunction with said template and guide tube for excising portions of the cancellous bone of said plateau coaxially with said guide tube and laterally thereof on the lines of said slots.

2. In a knee joint prosthesis, a tibial component for mounting on a tibial plateau which has been appropriately resected and trimmed in a manner removing as little bone as possible to provide:

a substantially flat upper surface defining a plateau on a plane normal to the axis of the intramedullary canal of said tibia to expose the cancellous bone centrally of said plateau, and to expose the upper rim of the relatively hard peripheral cortical wall;

a narrow cylindrical opening in the cancellous bone extending from said upper surface substantially down into the tibia on the axis of the intramedullary canal of the tibia; and, two lateral slots in said upper surface extending down into the cancellous bone of said tibia, said slots being in communication with and extending radially outwardly from said cylindrical opening into the areas of maximum hardness of the cancellous bone of said tibia in planes disposed at an angle of between about ten degrees and thirty degrees to the transverse plane of the joint which passes through the axis of said intramedullary canal respectively;

said tibial component comprising:

(a) a base plate having a thickness, and being contoured and shaped to approximate the size and shape of said plateau; said base plate further having posterior, left, right, and anterior edges; a top surface; and an under surface; said under surface being contoured so as to substantially match the contour of said plateau, and said top surface defining recessed areas adjacent the right and left edges of the base plate separated by an upwardly projecting area extending between said posterior and anterior edges of said base plate substantially centrally thereof, and flanked by upwardly projecting portions adjacent the posterior and anterior edges of the base plate, said base plate futher defining walls in its posterior edge forming an opening which provides an unobstructed path for the posterior cruciate ligament of said joint to pass upwardly for attachment to the anterior portion of the femur of said joint;

(b) means having a first and second surface and substantially the same peripheral contour as said base plate mounted on the top surface of said base plate such that said first surface is adapted to receive and support condylar portions of said joint, and said second surface defines a contour which substantially directly abuts the top surface of said base plate;

(c) a fixation pin on the under surface of said base plate aligned (relative to the contour of said base plate) with said cylindrical opening in said plateau, and dimensioned to fit therein, when said base plate is mounted on, and in abutment with, said trimmed and prepared plateau;

(d) means on the under surface of said base plate for anchoring said base plate against both shear and rotational forces relative to said plateau comprising a pair of elements dimensioned to fit into, and substantially fill, the cross sectional area of said slots, each element having a proximal end, a distal end, a top edge, a bottom edge, a proximal portion adjacent said proximal end, and a distal portion adjacent its distal end, said elements being respectively affixed along their top edges to the underside of the base plate and along their proximal ends to said fixation pin so as to extend radially outwardly from the fixation pin under the recessed areas of said base plate at angles corresponding to the angles at which said slots extend from said cylindrical opening in said plateau so that said elements fit within said slots when said base plate is mounted on, and in abutment with, said trimmed and prepared plateau, the maximum height of the proximal portion between the top edge and the bottom edge of each said element being substantially smaller than the maximum height of the distal portion between the top edge and the bottom edge of each said element, whereby an extremely stable and strong tibial component is provided having a minimum vertical height, but maximum strength and wear characteristics.

3. The tibial component of claim 2 further characterized by said base plate being composed of a metallic material.

4. The tibial component of claim 3 further characterized by the metallic material being selected from the group comprising cobalt-chromium-molydenum alloy and titanium-6aluminum-4vanadium alloy.

5. The tibial component of claim 2 further characterized by the means to support condylar portions of the joint being composed of high molecular weight polyethylene.

6. The tibial component of claim 2 further characterized by the bottom edge of each of said anchoring elements defining a single continuous and smooth contour.

7. The tibial component of claim 2 further characterized by means on said top surface of said base plate and on said second surface of said condylar portion supporting means for removably affixing said supporting means to said top surface.

8. The tibial component of claim 7 further characterized by said means for removably affixing said supporting means to said top surface comprising anteriorly extending flanges disposed along the top edge of each of the posterior lateral raised portions adjacent the recessed areas of said top surface, an upwardly extending wall portion arising from the central raised portion along the anterior edge of the base plate having a posteriorly extending flange extending from the top edge of said upwardly extending wall, posteriorly extending flanges extending from the posterior surfaces of said support means which abut the anterior surface of said posterior lateral raised portions adjacent said recessed areas adapted to engage the anteriorly extending flanges of said posterior lateral raised portions, and a flexible locking member disposed on the anterior edge of said support means adjacent said upwardly extending wall portion from the central raised portion of said base plate adapted to engage the posteriorly extending flange thereof in a snap fit relation.

* * * * *